US008241743B2

(12) United States Patent
Brennan (10) Patent No.: US 8,241,743 B2
(45) Date of Patent: *Aug. 14, 2012

(54) DISPERSIBLE NONWOVEN WEBS AND METHODS OF MANUFACTURE

(75) Inventor: Jonathan Paul Brennan, Sharonville, OH (US)

(73) Assignee: The Proctor & Gamble Company, Cincinnati, OH (US)

( * ) Notice: Subject to any disclaimer, the term of this patent is extended or adjusted under 35 U.S.C. 154(b) by 790 days.

This patent is subject to a terminal disclaimer.

(21) Appl. No.: 11/303,412

(22) Filed: Dec. 16, 2005

(65) Prior Publication Data
US 2006/0135018 A1 Jun. 22, 2006

Related U.S. Application Data

(60) Provisional application No. 60/638,696, filed on Dec. 22, 2004.

(51) Int. Cl.
*D06N 7/04* (2006.01)
*B32B 3/00* (2006.01)
*B32B 3/28* (2006.01)
*B32B 5/14* (2006.01)
*B32B 7/02* (2006.01)
*D21H 11/00* (2006.01)
*D21H 13/00* (2006.01)

(52) U.S. Cl. ........ 428/327; 442/327; 162/109; 162/116; 428/141; 428/156; 428/167; 428/170; 428/218

(58) Field of Classification Search ............... 15/104.93, 15/209.1; 28/165, 104, 105; 156/229; 160/169; 162/112, 204, 134, 135, 158, 164.1, 164.3, 162/206, 115; 206/812; 264/145, 518, 546; 424/404, 408; 428/154, 192, 196, 219, 340, 428/409, 43, 81, 195.1, 120, 141, 198, 311.11, 428/311.51, 311.71, 343, 352, 354, 327; 442/1, 327, 373, 411, 96, 118, 121, 123, 442/153, 408, 409, 415, 58, 151, 65, 154, 442/334, 336, 337, 394, 398; 510/137, 157; 604/364, 365, 382, 376, 378, 383, 385.01, 604/394, 368–370; 83/861, 863, 864; 425/154
See application file for complete search history.

(56) References Cited

U.S. PATENT DOCUMENTS
3,563,241 A * 2/1971 Evans et al. ................. 604/364
(Continued)

FOREIGN PATENT DOCUMENTS
WO WO 02/066089 A2 8/2002
(Continued)

OTHER PUBLICATIONS
Fuerstenau, Maurice & Han, Kenneth. (2003) Principles of Mineral Processing. Society for Mining, Metallurgy, and Exploration, Inc.: Littleton, CO. p. 125.*
(Continued)

*Primary Examiner* — David R Sample
*Assistant Examiner* — Nicole Gugliotta
(74) *Attorney, Agent, or Firm* — Christian M. Best; C. Brant Cook (57) ABSTRACT

Nonwoven webs that are comprised of non-thermoplastic fibers, have good in-use strength, and that disperse or break apart when subjected to agitation in water are disclosed. Premoistened wipes comprising such webs are also disclosed. The method of making the nonwoven webs is described as providing the webs with discrete compressed sites that form lines of weakness, such that the web may fail in tension along the lines of weakness when the web is subjected to a force less than the maximum force of the uncompressed regions of the web.

13 Claims, 10 Drawing Sheets

U.S. PATENT DOCUMENTS

| | | | |
|---|---|---|---|
| 3,798,120 A * | 3/1974 | Enloe et al. | 162/112 |
| 3,855,046 A | 12/1974 | Hansen et al. | |
| 3,881,210 A * | 5/1975 | Drach et al. | 15/104.93 |
| 4,755,421 A | 7/1988 | Manning et al. | |
| 5,137,600 A * | 8/1992 | Barnes et al. | 162/115 |
| 5,383,778 A | 1/1995 | Schulz | |
| 5,490,902 A | 2/1996 | Schulz | |
| 5,628,097 A * | 5/1997 | Benson et al. | 28/165 |
| 5,629,081 A * | 5/1997 | Richards et al. | 442/96 |
| 5,658,639 A | 8/1997 | Curro et al. | |
| 5,725,821 A | 3/1998 | Gannon et al. | |
| 5,761,982 A * | 6/1998 | Abt et al. | 83/861 |
| 5,935,880 A * | 8/1999 | Wang et al. | 442/65 |
| 6,013,349 A | 1/2000 | Takeuchi et al. | |
| 6,093,665 A | 7/2000 | Sayovitz et al. | |
| 6,127,593 A | 10/2000 | Bjorkquist et al. | |
| 6,190,502 B1 | 2/2001 | Takeuchi et al. | |
| 6,361,784 B1 | 3/2002 | Brennan et al. | |
| 6,383,958 B1 * | 5/2002 | Swanson et al. | 442/151 |
| 6,432,272 B1 * | 8/2002 | Hollenberg et al. | 162/204 |
| 6,433,245 B1 | 8/2002 | Bjorkquist et al. | |
| 6,544,912 B1 | 4/2003 | Tanio et al. | |
| 6,613,954 B1 * | 9/2003 | Horney et al. | 604/364 |
| 6,670,521 B2 * | 12/2003 | Noda et al. | 604/364 |
| 6,713,159 B1 * | 3/2004 | Blenke et al. | 428/195.1 |
| 6,749,718 B2 | 6/2004 | Takai et al. | |
| 2002/0022427 A1 | 2/2002 | Curro et al. | |
| 2002/0177827 A1 | 11/2002 | Noda et al. | |
| 2004/0198114 A1 | 10/2004 | Barnholtz et al. | |

FOREIGN PATENT DOCUMENTS

| | | | |
|---|---|---|---|
| WO | WO 2006/004871 A1 | 1/2006 | |

OTHER PUBLICATIONS

Hutten, Irwin. (2007) Handbook of Nonwoven Filter Media. Elsevier Ltd.: Oxford. pp. 204-205.*

PCT International Search Report dated Jun. 28, 2006, 3 pages.

U.S. Appl. No. 11/166,925, filed Jun. 23, 2005, Sheehan et al.

* cited by examiner

Fig. 10 ns
DISPERSIBLE NONWOVEN WEBS AND METHODS OF MANUFACTURE

CROSS REFERENCE TO RELATED APPLICATIONS

This application claims the benefit of U.S. Provisional Application No. 60/638,696, filed Dec. 22, 2004.

FIELD OF INVENTION

The present invention relates to dispersible non-woven webs and articles made therefrom. The nonwoven webs may form disposable articles such as wet wipes.

BACKGROUND OF INVENTION

Non-woven webs are currently used in a variety of disposable articles including, but not limited to, feminine hygiene products, diapers, training pants, adult incontinence products and wipes. Disposable wipes comprising non-woven webs are widely used by consumers to clean surfaces, such as glass and ceramic tile, as well to clean the skin of children and adults. Pre-moistened or wet wipes are also known.

Disposable articles, such as wipes, can be discarded by flushing them down a conventional toilet into a sewage or septic system where they may subsequently degrade. This disposal method is convenient and discrete. However, it is desirable that a disposable article, once flushed, readily disperses or breaks apart so that it can pass through a conventional toilet and plumbing system without creating blockages. It is also desirable that the disposable article have adequate structural integrity for its intended use. The balance between dispersibility and in-use strength may be difficult to achieve, particularly when a disposable article is to be used in a pre-moistened application that requires long-term wet storage stability, such as a wet wipe.

Examples of nonwoven webs, methods of manufacturing nonwoven webs, as well as articles comprising nonwoven webs may be found in the art. See, for example: U.S. Pat. Nos. 6,190,502 and 6,544,912; U.S. Patent Application Publication 2002/0177827 A1; and the wet wipes currently marketed under the "Just for Kids™" and "Kandoo™" brand names.

SUMMARY OF INVENTION

The present invention provides improvements in non-woven webs and the wipes comprising nonwoven webs. In one embodiment, the invention is directed to nonwoven webs having good in-use strength, which disperse or break apart when subjected to agitation in water. In another embodiment, the invention is directed to a process for increasing the dispersibility of nonwoven webs. In yet another embodiment, the invention is directed to wipes comprising the nonwoven webs of the present invention.

In some embodiments, nonwoven webs of the present invention may comprise non-thermoplastic fibers, wherein at least about 20% of the non-thermoplastic fibers have a fiber length of at least about 18 mm. The webs may further comprise: (a) a plurality of discrete compressed sites that are less than about 2.5 square millimeters in area and separated by an edge to edge distance of no more than about 10 millimeters from the nearest adjacent discrete compressed site; (b) lines of weakness; and (c) discrete uncompressed regions characterized by an elongation at maximum force in the machine direction and an elongation at maximum force in the cross direction. The (a) plurality of discrete compressed sites may form the (b) lines of weakness and the lines of weakness may be arranged to substantially bound and define the (c) discrete uncompressed regions. When the webs are subjected to a force less than the maximum force of the (c) discrete uncompressed regions, the webs at least partially fail in tension along the (b) lines of weakness.

In some embodiments, a process for increasing the dispersibility of nonwoven webs comprising non-thermoplastic fibers, wherein at least about 20% of the non-thermoplastic fibers have a fiber length of at least about 18 mm, may comprise the following steps. A compressive stress of at least about 200 Newtons per square millimeter is applied to the web. The compressive stress imparts the web with: (a) a plurality of discrete compressed sites that are less than about 2.5 square millimeters in area and separated by an edge to edge distance of no more than about 10 millimeters from the nearest adjacent discrete compressed site; (b) lines of weakness; and (c) discrete uncompressed regions characterized by an elongation at maximum force in the machine direction and an elongation at maximum force in the cross direction. The (a) plurality of discrete compressed sites form the (b) lines of weakness and the lines of weakness are arranged to substantially bound and define the (c) discrete uncompressed regions. When the web is subjected to a force less than the maximum force of the (c) discrete uncompressed regions, the web at least partially fails in tension along the (b) lines of weakness.

In some embodiments, pre-moistened carded spunlaced nonwoven webs of the present invention comprise non-thermoplastic fibers selected from the group consisting of rayon fibers, pulp fibers and combinations thereof, wherein at least about 20% by weight of the non-thermoplastic fibers have a length of at least about 38 millimeters. The webs may further comprise: (a) a plurality of discrete compressed sites that are less than about 2.5 square millimeters in area and separated by an edge to edge distance of no more than about 10 millimeters from the nearest adjacent discrete compressed site; (b) lines of weakness; and (c) discrete uncompressed regions, wherein the discrete uncompressed regions characterized by an elongation at maximum force in the machine direction and an elongation at maximum force in the cross direction. The (a) plurality of discrete compressed sites may form the (c) lines of weakness and the lines of weakness may be arranged to substantially bound and define the (c) discrete uncompressed regions. When the webs are subjected to a cross direction force less than about 8 Newtons, the webs at least partially fail in tension along the (b) lines of weakness.

BRIEF DESCRIPTION OF DRAWINGS

The features, aspects and advantages of the present invention will become better understood with reference to the following description, appended claims and accompanying drawings where:

DETAILED DESCRIPTION OF INVENTION

Definitions

"Fiber" as used herein, refers to a unit which forms the basic element of the web disclosed herein.

"Nonwoven web" as used herein, refers to a layer or layers of fibers that are laid and bonded via nonwoven manufacturing processes known in the art. "Wipe" as used herein refers to an article that is comprised of one or more layers of web.

"Liquid composition" as used herein, refers to any liquid, including, but not limited to a pure liquid such as water, a colloid, an emulsion, a suspension, a solution and mixtures thereof. The term "aqueous solution" as used herein, refers to a solution that is at least about 20%, at least about 40%, or even at least about 50% water by weight, and is no more than about 95%, or no more than about 90% water by weight.

"Pre-moistened wipe" as used herein may refer to a wipe which is wetted, or is comprised of a portion that is wetted, with a liquid composition prior to use by the consumer. "Pre-moistened wipe" may also refer to wipes that are wetted with a liquid composition prior to packaging, such as in a generally moisture impervious container or wrapper. Such pre-moistened wipes, which may also be referred to as "wet wipes" and "towelettes", may be suitable for use in cleaning babies, and may also find use in cleaning tasks related to persons of all ages. Such wipes may also be suitable for use in the application of substances to the body, including but not limited to make-up, skin conditioners, ointments, medications and mixtures thereof. Such wipes may also be of use for the cleaning or grooming of pets, or for the general cleansing of surfaces and objects, such as household kitchen and bathroom surfaces, eyeglasses, exercise and athletic equipment, automotive surfaces and the like.

"Compressive stress" as used herein, refers to the blunt force which, when applied to a web, produces "compressed sites". Compressive stress may not include shear force, which when applied to a web, cuts the fibers comprising the web. Without wishing to be bound by theory, it is believed that the blunt force has less impact on the in use strength of the web than shear force since it mainly weakens the fibers at the edge of the compressed site instead of cutting them. Compressive stress is measured in units of Newtons per square millimeter (N/mm$^2$).

"Compressed sites" as used herein, refers to areas of the web in which the fibers comprising the web are pressed together such that fibers are brought closer together in space as compared to the fibers that are located in the uncompressed regions. The compressed sites may have a higher fiber density as compared to the uncompressed regions.

"Uncompressed regions" as used herein, refers to those areas of the web that may not contain compressed sites. The fibers comprising the uncompressed regions of the web may substantially remain in an unaltered form after the web is subjected to compressive stress. "Substantially" is as an adverb which as used herein means being largely, but not wholly.

"Line of weakness" as used herein, refers to an imaginary line drawn to connect a compressed site or series of compressed sites with the nearest adjacent compressed site or nearest series of compressed sites respectively. The imaginary line may be straight or curved. When a web is subjected to a force less than the maximum force of its discrete uncompressed regions, the web fails in tension, or at least partially fails in tension, along the lines of weakness.

"Maximum force" as used herein, refers to the stretching force necessary to cause the integrity of a web or a portion of a web, to "fail in tension". The maximum force of a web may be measured by tensile testing in both the "cross direction" and the "machine direction" of the web. Maximum force is measured in the unit of Newtons (N).

"Elongation at maximum force" as used herein, refers to the longitudinal elongation of a web, or a portion of a web, when it is subjected to its maximum force.

"Edge" as used herein, refers to the line of transition between a compressed site and an uncompressed region as viewed with the naked eye.

"Edge to edge distance" as used herein, refers to the length of the shortest line that may be drawn between the edges of two adjacent discrete compressed sites when viewed with the naked eye.

"Adjacent" as used herein, refers to nearby but not touching.

As used herein, "dispersible" refers to a product which has the ability to exhibit visible changes after being flushed down a standard toilet and passed through a typical waste water system, which may include, but is not limited to, pumps, pipes, tanks, sieves, separation units and combinations thereof.

"Fail in tension" as used herein, refers to a failure to the integrity of the product visible to the naked eye, such as: holes, slits, shreds, breaking apart into smaller sections, dissolving or a combination thereof. Any visible change when the web is under force indicating weakening of the web may be regarded as failing in tension. Typically, the web will fail in tension along lines of weakness. "Partially fails in tension" as used herein, refers to when the failure of the integrity of the product is initiated.

"Binder" as used herein, refers to any compound added to the nonwoven web that may improve the strength of the web, yet that may disassociate from the web when subjected to the conditions encountered by the web during or after disposal. Such conditions may include, but are not limited to, large amounts of water, particular pHs, water with particular ion concentrations and combinations thereof. When the web comprising the binder is exposed to particular conditions, the binder may dissolve, for example. When the binder dissolves, the strength of the web may decrease and in turn the dispersibility of the web may increase. Binders, for example, may be water soluble, water-swellable and combinations thereof. Polyvinyl alcohol (PVOH) and EP919, which is a flushable, dispersible binder sold by Air Products of Allentown, Pa., USA, are non-limiting examples of binders. Further examples of binders may include, but are not limited to, sulfonic-acid modified PVOH, carboxylic-acid modified PVOH, and binders comprising at least one compound selected from the group consisting of a water-soluble organic salt, a water-soluble inorganic salt and a boron compound. A further non-limiting example of a binder may include water-insoluble or water-swellable carboxymethylcellulose. The solubility of carboxymethylcellulose may depend on its degree of etherification and pH, among other factors. In some embodiments of the present invention, the nonwoven webs may comprise binder in an amount from about 0.1% to about 10%, from about 0.5% to about 5%, or even from about 1% to about 2%.

When used herein in relation to material compositions, the terms "%", "percent", "weight percent" or "percent by weight" refer to the quantity by weight of a component as a percentage of the total weight, unless otherwise indicated.

As used herein with respect to webs, the term "machine-direction" or "MD" refers to the direction of web travel as the web is produced, for example on commercial nonwoven production equipment. Likewise, the term "cross-direction" or "CD" refers to the direction perpendicular to the machine direction and parallel to the general plane of the layered fibrous product and/or layered fibrous structure. With respect to individual wipes, the terms refer to the corresponding directions of the wipe with respect to the web used to produce the wipe. These directions are carefully distinguished herein, because the mechanical properties of a nonwoven web may differ depending on how the nonwoven web is oriented during testing. For example, tensile properties of a web may differ between the machine-direction and the cross-direction, due to the orientation of the constituent fibers, and other process-related factors.

"Comprising" as used herein, refers to the various components, ingredients or steps that may be conjointly employed in practicing the present invention. Accordingly, the term "comprising" may encompass the more restrictive terms "consisting essentially of" and "consisting of".

"Water soluble" as used herein, refers to a component that is soluble or otherwise dispersible (such as to provide a micellar solution) in water at a level of at least about 0.25 percent by weight at about 25 degrees Centigrade.

"Surfactant" as used herein, refers to materials which may preferably orient toward an interface. Classes of surfactants may include, but are not limited to: nonionic surfactants, anionic surfactants, cationic surfactants, amphoteric surfactants, zwitterionic surfactants and mixtures thereof.

"Emulsifier" and "solubilizer" may be interchangeably used herein, and refer to components that may reduce the tendency of one or more other components in a lotion composition to phase separate from the lotion.

"Co-surfactant" as used herein, refers to a component that may act as either a surfactant or an emulsifier/solubilizer.

"Organic water soluble polymer" as used herein, refers to an organic compound formed by the joining of smaller molecules, referred to as monomers. The term may be used to refer either to a macromolecule made up of a large number of monomers linked by covalent bonds, e.g., polypeptides, nucleic acids, polysaccharides, and plastics, or to a protein made up of several subunits linked by covalent or no covalent bonds, e.g., hemoglobin or IBM immunoglobulin.

DETAILED DESCRIPTION OF THE FIGURES

Figure 1A:
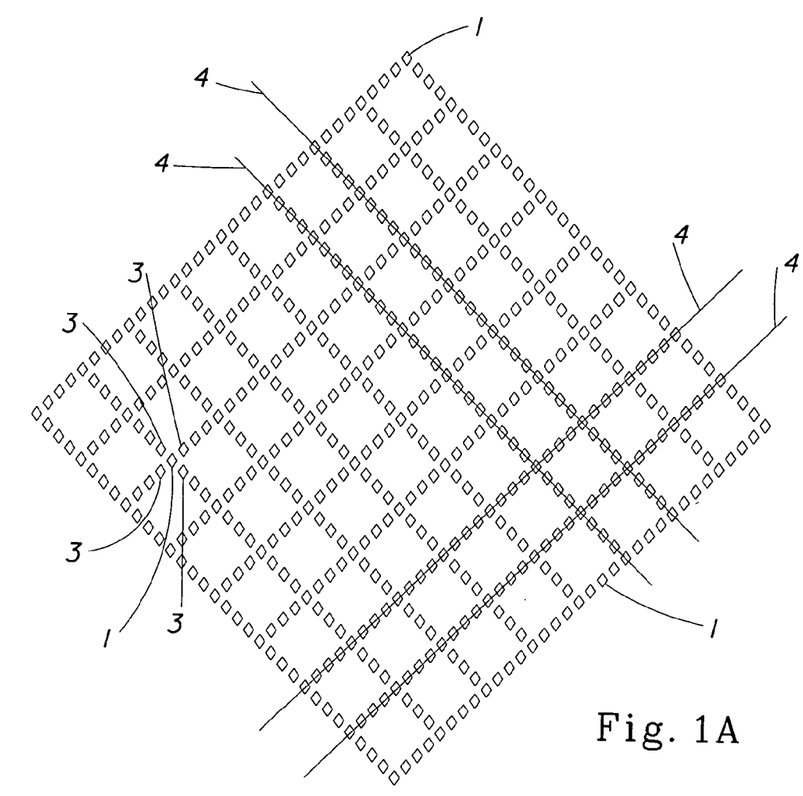
FIG. 1A is a view of one embodiment of a pattern which may be made by the plurality of discrete compressed sites.
Figure 1B:
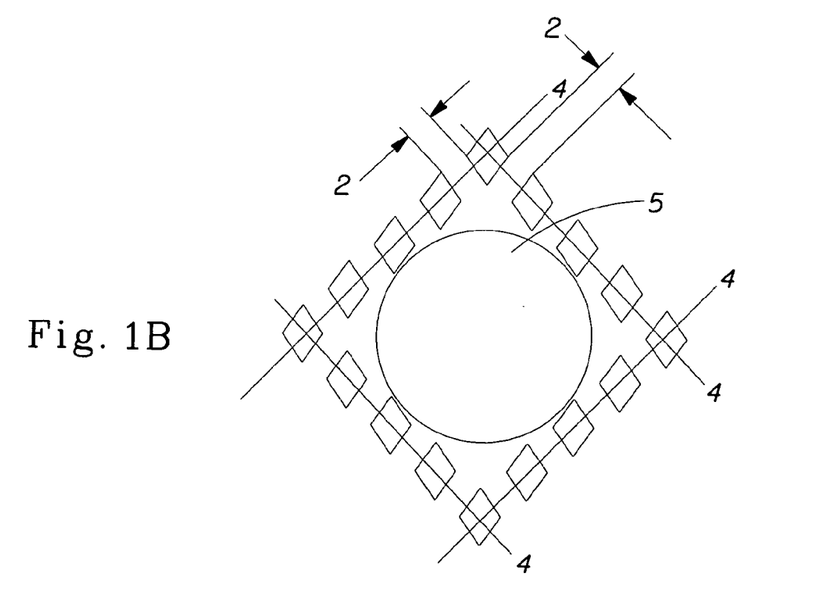
FIG. 1B is an enlarged view of a portion of the pattern shown in FIG. 1A.

FIG. 1A shows one embodiment of the plurality of discrete compressed sites comprising the nonwoven web of the present invention. The plurality of discrete compressed sites (1), which may take any shape as long as they are each less than about 2.5 mm$^2$ in area, less than about 1.5 mm$^2$ in area, or even less than about 0.6 mm$^2$ in area, and at least about 0.1 mm$^2$ in area, are shown in FIG. 1B as diamond-shaped. The discrete compressed sites may be separated by an edge to edge distance (2) from the nearest adjacent compressed sites (3). Lines of weakness (4) may be drawn to connect a compressed site or series of compressed sites with the nearest adjacent compressed site or sites, respectively. Lines of weakness may be arranged to substantially bound and define discrete uncompressed regions (5).

Figure 2:
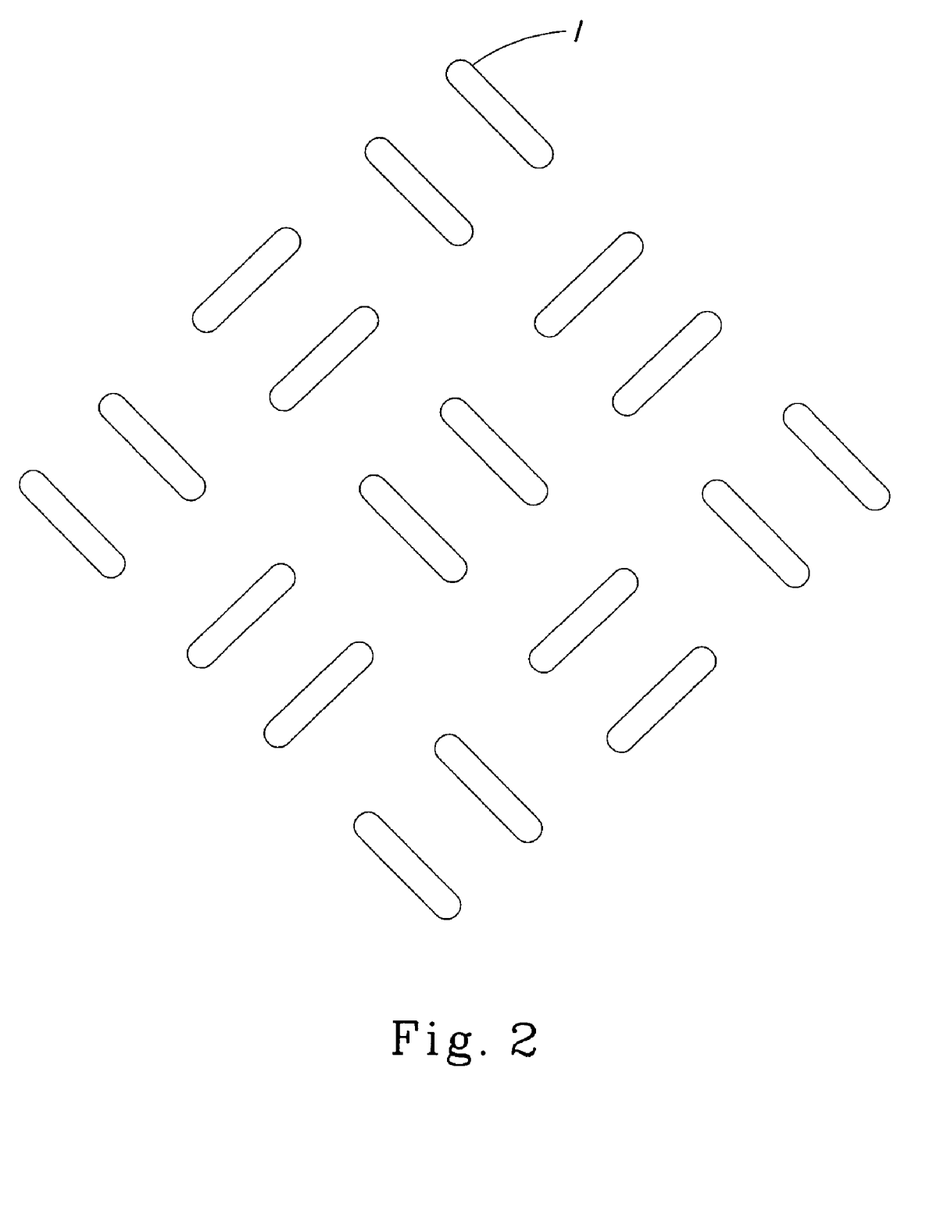
FIG. 2 is a view of another embodiment of a pattern, which may be made by the plurality of discrete compressed sites.

FIG. 2 shows a further embodiment of the plurality of discrete compressed sites.

Figure 3:
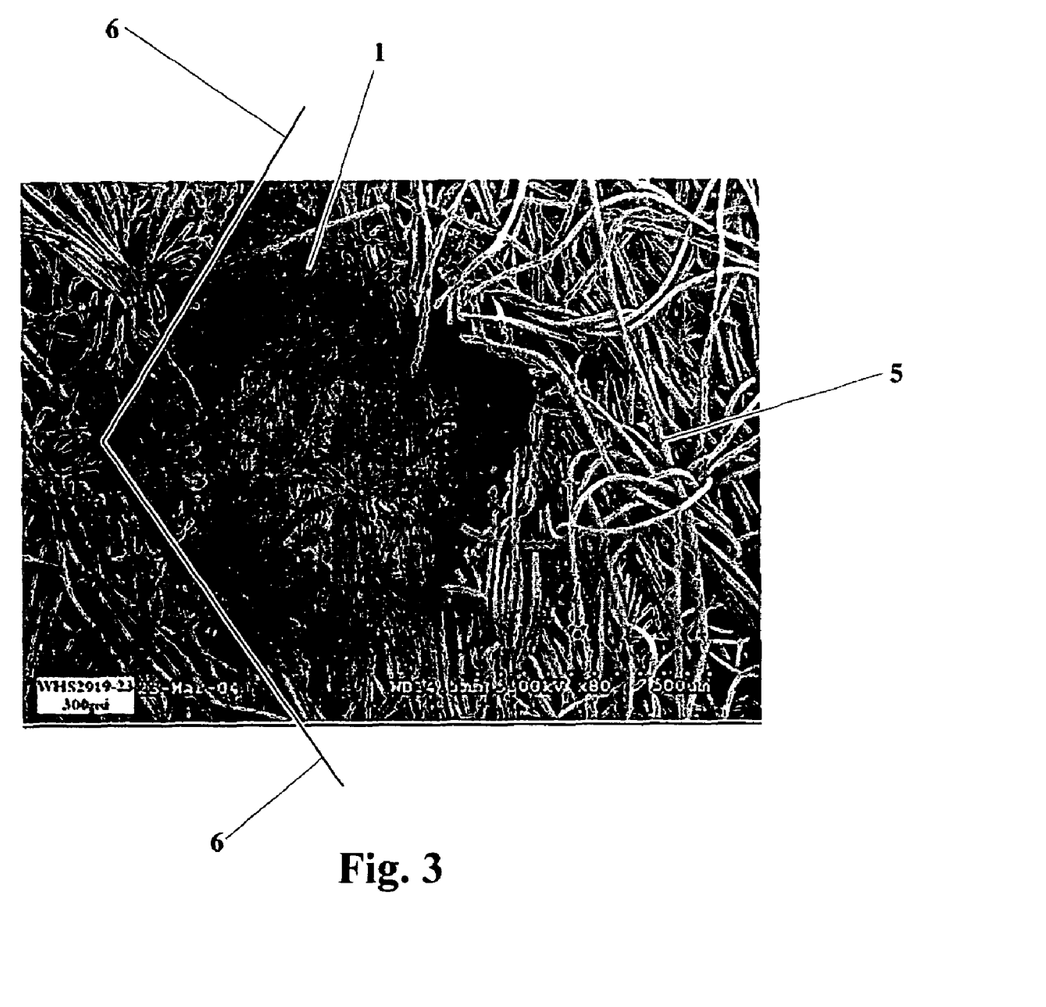
FIG. 3 is a scanning electron micrograph (SEM) of a 100% rayon carded spunlaced (i.e., hydroentangled) web as described herein.

FIG. 3 shows an SEM of a 100% rayon carded spunlaced web as described herein. The figure shows a portion of the web comprising a compressed site (1) and uncompressed regions (5). The edges (6) of the discrete compressed site may be seen at the interface between the compressed site and the uncompressed regions.

FIGS. 4-9 illustrate how one embodiment of the nonwoven webs comprising the discrete compressed sites of the present invention are different from the identical webs without the discrete compressed sites of the present invention. The embodiment is comprised of a carded spunlaced nonwoven web comprised of 100% rayon fibers (supplied by the Tenotex Company, of Terno d'Isola, Italy, under trade name of Tenolace™ FV60), wherein the web is pre-moistened with about 3 grams of a silicone-based emulsion per about 1 gram of dry web. The rayon fibers of this embodiment, which are about 40 mm in length and about 1.7 dtex, are supplied by the Lenzing Company, of Lenzing, Austria. Samples of both the web with and without the discrete compressed sites of the present invention are elongated in the machine direction by 30% at a rate of 25 millimeters per minute using a Synergie 400 tensile tester, from MTS Systems Corporation, Eden Prairie, Minn., USA.

Figure 4:
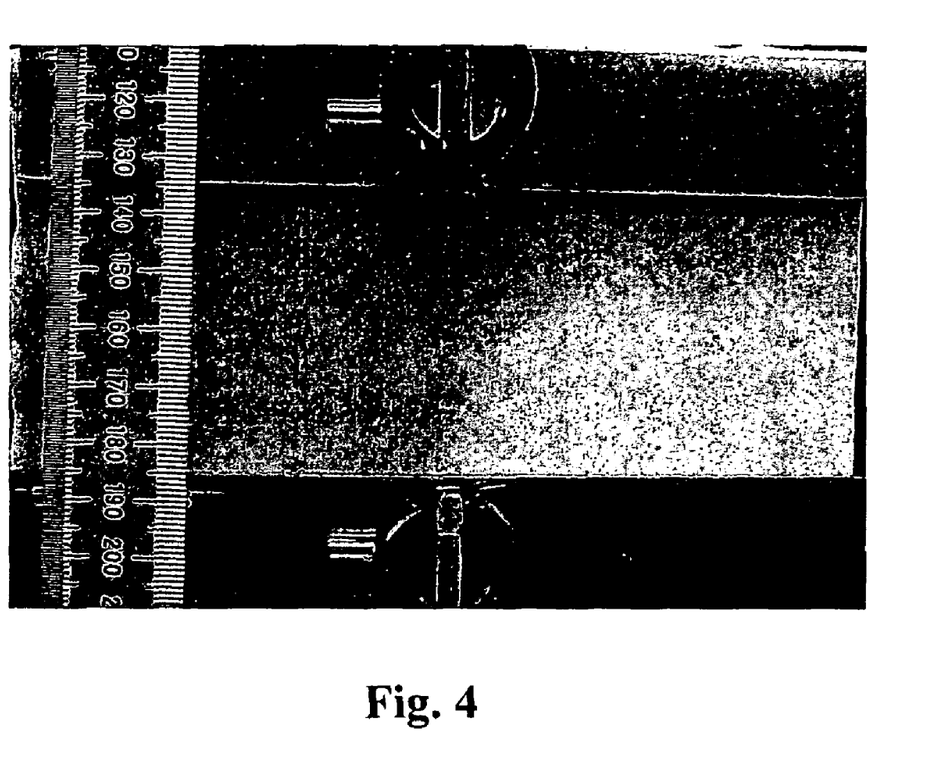
FIG. 4 is a view of a pre-moistened 100% rayon carded spunlaced web without the discrete compressed sites as described herein, before being subjected to elongation.
Figure 5:
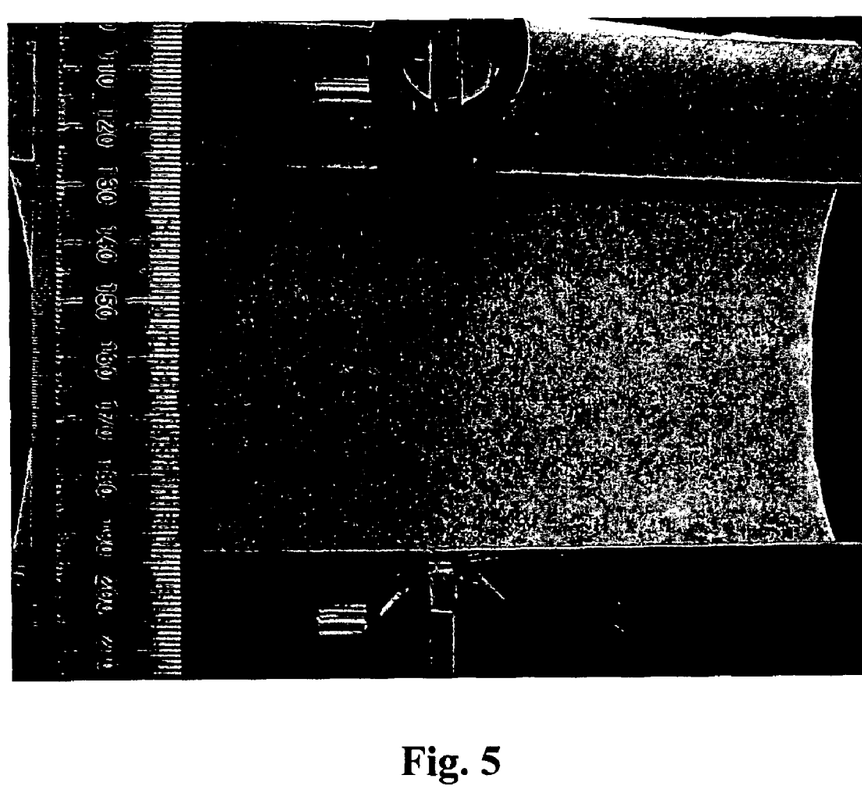
FIG. 5 is a view of a pre-moistened 100% rayon carded spunlaced web without the discrete compressed sites as described herein, after being subjected to about 30% elongation.

FIG. 4 shows the nonwoven web without discrete compressed sites before elongation. FIG. 5 shows the same web after elongation. Note that the web does not fail in tension.

Figure 6:
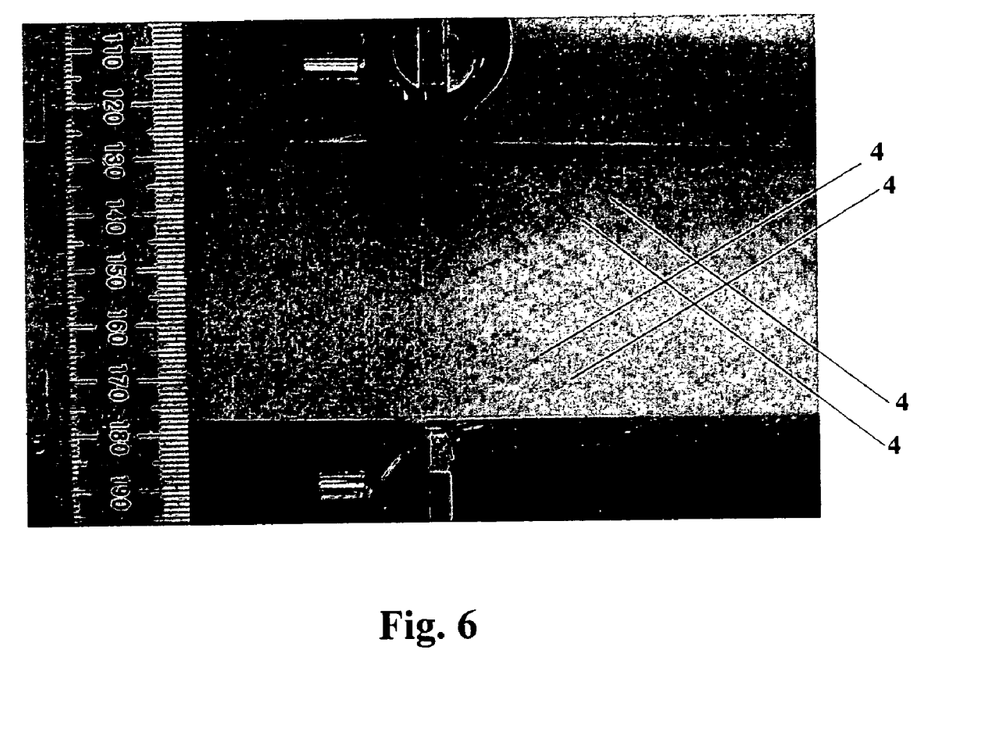
FIG. 6 is a view of a pre-moistened 100% rayon carded spunlaced web as described herein, comprised of a plurality of discrete compressed sites arranged in the pattern shown in FIG. 1A, before being subjected to elongation.
Figure 7:
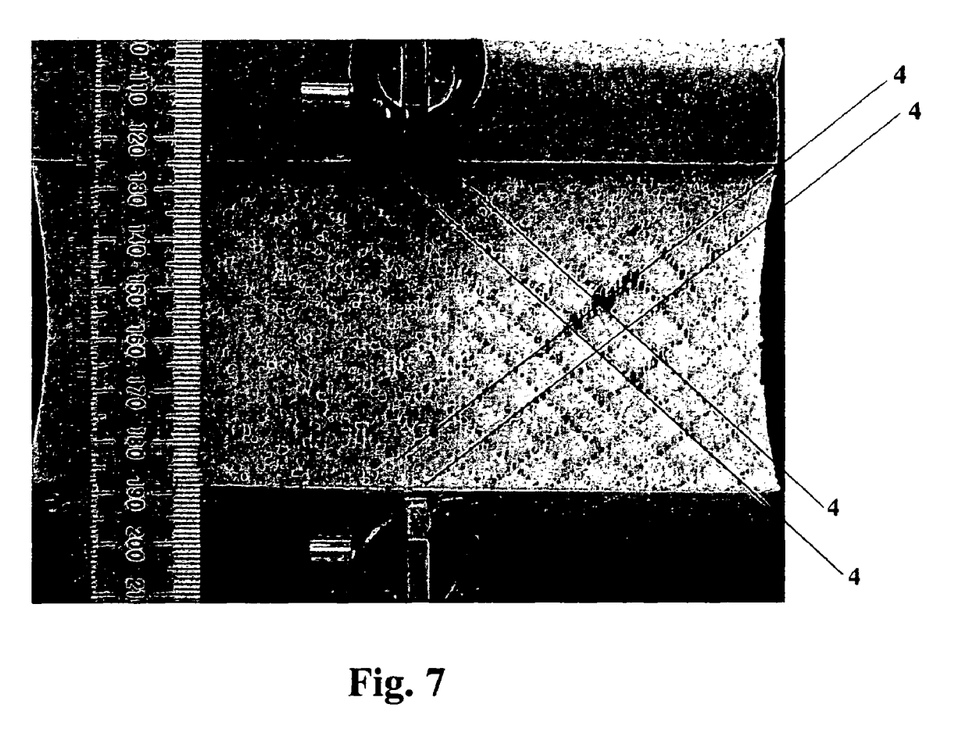
FIG. 7 is a view of a pre-moistened 100% rayon carded spunlaced web as described herein, comprised of a plurality of discrete compressed sites arranged in the pattern shown in FIG. 1A after being subjected to about 30% elongation.

FIG. 6 shows the nonwoven web with discrete compressed sites in the pattern shown in FIG. 1A before elongation. FIG. 7 shows the same web after elongation. Note that the web fails in tension along the lines of weakness (4).

Figure 8:
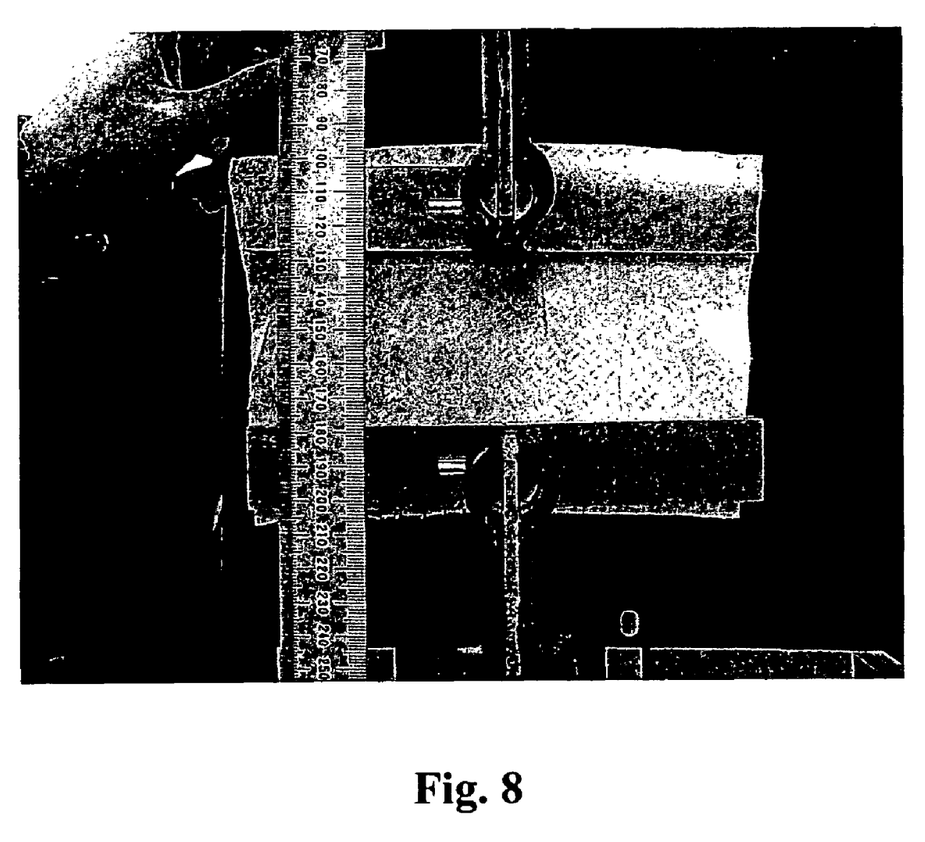
FIG. 8 is a view of a pre-moistened 100% rayon carded spunlaced web as described herein, comprised of a plurality of discrete compressed sites arranged in the pattern shown in FIG. 2 before being subjected to elongation.
Figure 9:
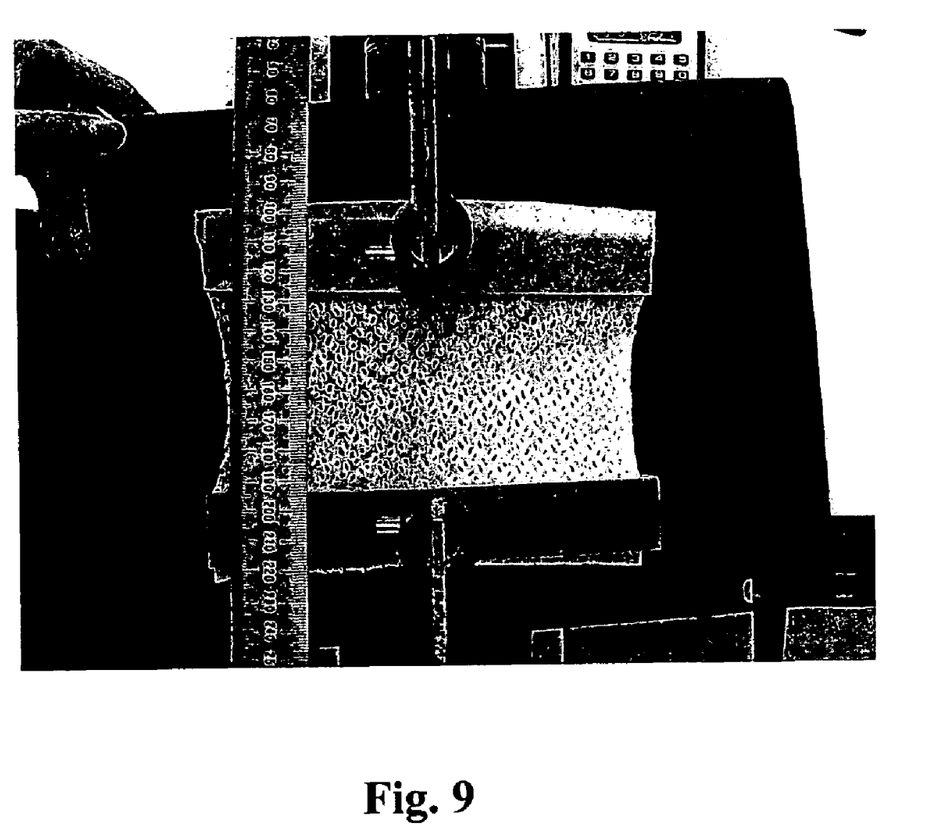
FIG. 9 is a view of a pre-moistened 100% rayon carded spunlaced web as described herein, comprised of a plurality of discrete compressed sites arranged in the pattern shown in FIG. 2 after being subjected to about 30% elongation.

FIG. 8 shows the nonwoven web with the discrete compressed sites in pattern shown in FIG. 2 before elongation. FIG. 9 shows the same web after elongation. Note that the web fails in tension.

Without wishing to be bound by theory, FIGS. 4-9 illustrate the effectiveness of the compressed sites in creating lines of weakness.

Nonwoven Web

The nonwoven webs of the present invention comprise man-made fibers, natural fibers and combinations thereof, and may or may not be biodegradable. Non-limiting examples of man-made fibers include: rayon, which in turn includes but is not limited to viscose, lyocell and mixtures thereof; polyhydroxyalkanoates; polylactic acid; polyester; and mixtures thereof. Non-limiting examples of natural fibers include: pulp, cotton, wool, silk, jute, linen, ramie, hemp, flax, camel hair, kenaf, and mixtures thereof. Non-thermoplastic fibers that are of use in the present invention are selected from the group consisting of: rayon, which in turn includes but is not limited to viscose, lyocell and mixtures thereof; pulp; cotton; wool; silk; jute; linen; ramie; hemp; flax; camel hair; kenaf; and mixtures thereof.

Fiber length is measured prior to the fiber laying and bonding processes. The fibers of use in the present invention may have a fiber length of: at least about 18 mm; at least about 20 mm; at least about 25 mm; at least about 30 mm; at least about 35 mm; or even at least about 38 mm. The fibers of use in the present invention may be essentially continuous and have a fiber length that is theoretically infinite.

The fibers of use in the present invention may have an average fiber decitex (dtex) of at least about 0.8 dtex, at least about 1 dtex, at least about 1.2 dtex, or even at least about 1.5 dtex. The fibers may have an average decitex of less than about 8 dtex, less than about 5 dtex, or even less than about 2 dtex.

In one embodiment of the present invention, the nonwoven webs may comprise from about 20% to about 80% rayon fibers and from about 80% to about 20% of pulp fibers. In another embodiment, the nonwoven webs may comprise from about 30% to about 70% rayon fibers and from about 70% to about 30% pulp fibers. In another embodiment, the nonwoven webs may comprise from about 40% to about 60% rayon fibers and from about 60% to about 40% pulp fibers. In yet another embodiment, the nonwoven webs may comprise about 60% rayon fibers and about 40% pulp fibers.

The nonwoven web may be manufactured via any number of processes. In general, processes currently known for making nonwoven webs may comprise two steps: fiber laying and fiber bonding. Fiber laying steps known in the art include, but are not limited to, spunlaying, meltblowing, carding, airlaying, wetlaying and combinations thereof, of the fibers comprising the web. Fiber bonding steps known in the art include, but are not limited to, spunlacing (or hydroentanglement), cold calendering, hot calendering, air thru bonding, chemical bonding, needle punching and combinations thereof.

The nonwoven webs of the present invention may be manufactured via carded spunlacing processes that utilize high amounts of relatively long fibers, which may be greater than at least about 18 mm in length. By using relatively long fibers, the nonwoven webs may be strong and soft, cloth-like, flexible and combinations thereof. Providing the nonwoven webs with the discrete compressed sites of the present invention, may result in nonwoven webs which retain good in-use strength, yet that have increased dispersibility.

The nonwoven webs of the present invention may have basis weights ranging from about 5 to about 200 grams per square meter (gsm), from about 10 to about 175 gsm, from about 30 to about 150 gsm, from about 20 to about 100 gsm, from about 30 to about 70 gsm, or even from about 40 to about 60 gsm.

Discrete Compressed Sites

The nonwoven webs of the present invention comprise discrete compressed sites. The discrete compressed sites may take any shape and each of the sites may have an area of less than about 2.5 square millimeters ($mm^2$). The discrete compressed sites may be randomly situated on the web or may form a pattern. Examples of patterns include, but are not limited to, the patterns shown in FIGS. 1A and 2, as well as variations thereof.

To impart discrete compressed sites to the nonwoven web, any method of applying compressive stress to the web may be used. Methods of applying compressive stress to the web include, but are not limited to, stamping, pressing, cold calender rolling, heated calender rolling and combinations thereof. The compressive stress may smash or compress the fibers with a blunt force, in contrast to other methods of applying stress in which the fibers are sheared or cut with a sharp edge.

Without wishing to be bound by theory, it is presumed that as a result of the compressive stress, the discrete compressed sites may have a higher fiber density as compared to the density of the uncompressed regions of the web. The uncompressed regions of the web may retain substantially the same density that the web has before it is subjected to the compressive stress.

After application of compressive stress to the nonwoven webs of the present invention, the discrete compressed sites may comprise less than about 20%, less than about 19%, less than about 17%, or even less than about 13% of the total web surface area. The percentage of total web surface area that may comprise discrete compressed sites is limited to less than about 19% in order to retain good in-use strength. For instance, if the web is to be used in a pre-moistened wipe application, particularly as a "pop-up wipe" (described below), it should be remain strong enough to withstand the dispensing process.

After application of compressive stress to the nonwoven webs of the present invention, the discrete compressed sites may comprise more than about 2%, more than about 3%, or even more than about 5% of the total web surface area. The percentage of total web surface area that may comprise the discrete compressed sites is greater than at least about 2% in order to weaken the web sufficiently such that it may fail along the lines of weakness when subjected to forces encountered by the web during or after disposal.

To illustrate how varying the amount of compressive stress applied to the web of the current invention may affect the web's tensile strength, the following experiment is performed. A sample of a 100% rayon carded spunlaced substrate is compressed at five different levels of compressive stress via an arrangement of a smooth calender roller and a patterned calender roller at ambient temperature. The pattern on the roller is the same as that shown in FIG. 1A, and has a total raised surface area of about 12.6%. The compressive stress applied to the substrate is calculated by dividing the total force by the compression area of the patterned roller, as shown in the sample calculation in Table 1, and is based on the assumption that the entire load is transferred though the raised area of the patterned roller. After compression, a silicone based liquid composition is applied to the substrates at a rate of about 3 grams of liquid composition to about 1 gram of dry substrate. Samples are cut in 50 mm wide strips and tested for tensile strength using EDANA method 20.2-89 in both the cross direction and machine direction. The results of the experiment are summarized in Table 2.

TABLE 1

Calendering Compressive Stress Sample Calculation

| | English | Metric |
|---|---|---|
| Cylinder Diameter | 4 [in] | 101.6 [mm] |
| Total Cylinder Area | 12.6 [$in^2$] | 8107.3 [$mm^2$] |
| Cylinder Pressure | 300 [psi] | 2.0684 [$N/mm^2$] |
| Cylinder Force | 3770 [lb] | 16769.5 [N] |
| Number of Cylinders | 2 | 2 |
| Total Force | 7540 [lb] | 33539.0 [N] |
| Roll Face Width | 16 [in] | 406.4 [mm] |
| PLI Loading | 471 [pli] | 82.5 [N/mm] |
| Total Raised Surface Area | 12.6% [%] | 12.6% [%] |
| Compression Width | 0.063 [in] | 1.5875 [mm] |
| Compression Area | 0.126 [$in^2$] | 81.3 [$mm^2$] |
| Compressive Stress | 59840 [psi] | 413 [$N/mm^2$] |

TABLE 2

Influence of Compressive Stress on Tensile Strength
of a 100% Rayon Carded Spunlaced Web

| Embossing Cylinder Pressure [psi] | Compressive Stress [N/mm$^2$] | MD Maximum Force [N] | MD Elongation at Maximum Force [%] | CD Maximum Force [N] | CD Elongation at Maximum Force [%] |
|---|---|---|---|---|---|
| 0 | 0.0 | 46.1 | 45.51 | 16.8 | 98.51 |
| 150 | 206 | 42.2 | 40.97 | 12.8 | 95.8 |
| 200 | 275 | 9.4 | 30.44 | 6.3 | 86.9 |
| 250 | 344 | 8.2 | 30.09 | 3.6 | 71.3 |
| 300 | 413 | 5.8 | 25.73 | 3.8 | 85.6 |
| 350 | 481 | 5.7 | 26.91 | 3.7 | 76.0 |

The results in Table 2 illustrate the effect that compressive stress may have on the tensile strength of a nonwoven web. Tensile strength is measured as the MD maximum force and as the CD maximum force. Both the MD and CD maximum forces decrease as the compressive stress used to make the web is increased. Without wishing to be bound by theory, it is believed that by increasing the compressive stress, the fibers comprising the web are increasingly weakened, which in turn, decreases the maximum force necessary to cause the web to fail in tension.

As seen in Table 2, when 0 N/mm$^2$ (which corresponds to an untreated web) and 206 N/mm$^2$ of compressive stress is applied to the web, the web is characterized by relatively high MD and CD maximum forces. Once the compressive stress applied to the web reaches 275 N/mm$^2$ and above (344, 413, or 481 N/mm$^2$), the MD and CD maximum forces significantly decrease. In this example, once the compressive stress has reached 275 N/mm$^2$, the web may experience selective breaking and/or weakening of the fibers at the edges of compressed regions (6) under a relatively low MD or CD maximum force of 10 N or lower. The breaking and/or weakening of the fibers may cause failure in tension along the lines of weakness. Although it may be desirable to have a nonwoven web which fails in tension under relatively low MD and/or CD maximum forces to aid in dispersibility, it may not be desirable to have the forces so low as to produce a web with insufficient in-use strength, particularly when the web is to be pre-moistened. Therefore, it may be desirable to balance the MD and CD maximum forces for both dispersibility and in-use strength. For example, in one embodiment of the present invention, a nonwoven web with discrete compressed sites may have an MD maximum force of from about 4 N to about 16 N, and a CD maximum force of from about 2 N to about 8 N. In a further embodiment, a nonwoven web may be imparted with discrete compressed sites at the lowest compressive stress necessary to lower the MD and CD maximum forces into the desired ranges.

It may further be noted from Table 2 that as the compressive stress used to impart the nonwoven web with discrete compressed sites increases, the MD and CD elongation at the respective MD and CD maximum forces decrease. In this particular example, both the MD and CD elongations are markedly reduced at compression forces equal to or greater than 275 N/mm$^2$. Without wishing to be bound by theory, it is believed that the reduction in maximum force may result from the selective breaking and/or weakening of fibers at the edge of the compressed regions (6).

Figure 10:
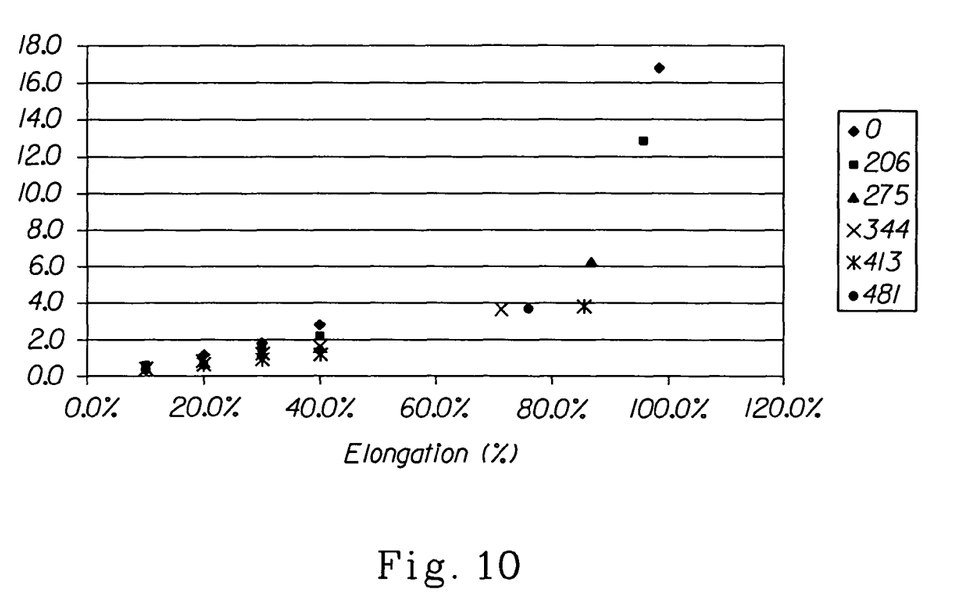
FIG. 10 is a plot of the cross directional force applied to 100% rayon carded spunlaced nonwoven webs versus the percentage elongation of the web when subjected to tensile testing.

FIG. 10 is a graph containing a plot of the CD force versus the CD elongation for nonwoven webs subjected to increasing levels of compressive stress; the data is generated as follows.

A 100% rayon carded spunlaced web is cut into six samples. Five of the samples are provided with the discrete compressed sites of the present invention using a different level of compressive stress for each sample, namely: 206, 275, 344, 413 and 481 N/mm$^2$. The remaining sample is not subjected to a compressive stress (0 N/mm$^2$). Each of the samples is then subjected to tensile testing as described above, using a "CD force", which is a force that is applied to the sample in its CD direction. Elongation of each sample is measured until it fails in tension. The resulting data is plotted as in FIG. 10.

It is apparent from FIG. 10 that similar amounts of CD force are necessary to elongate all of the samples to about 40%; 40% elongation before failure in tension is desirable for nonwoven webs used in pre-moistened applications. It is also apparent that the nonwoven webs that are treated with higher compressive stress, 275, 344, 413 and 481 N/mm$^2$, require less force to be elongated beyond 40% as compared to webs that have been treated with lower or no compressive force, 206 and 0 N/mm$^2$, respectively. The latter two webs require significantly higher CD forces for elongation beyond 40%.

Nonwoven webs which require significantly higher forces for elongation may be undesirable for use in wipe applications, because although they may not fail in tension and/or in planar shear when subjected to typical in-use forces (about 2 to 10 N), they may not fail in tension and/or in planar shear when flushed. Without wishing to be bound by theory, it is believed that once flushed, these webs may continue to elongate, and twist or rope upon themselves, making them stronger, and making it more likely for them to get caught in and to clog a plumbing system. In contrast, when the nonwoven webs of the present invention are flushed, they may fail in tension and/or planar shear along the lines of weakness (see FIG. 7 for example), and the discrete uncompressed regions may substantially separate into discrete pieces, which may readily pass through the plumbing system.

Since the typical size of an orifice in a plumbing system is about 5 centimeters (cm) or 50 mm in diameter, it is advantageous for the discrete pieces of the present invention to comprise two dimensional areas that are small enough so that the pieces may readily pass through the system. The discrete pieces of the present invention may have a maximum two dimensional area of: about 625 square millimeters (mm$^2$), about 500 mm$^2$, about 125 mm$^2$, or even about 100 mm$^2$. The discrete pieces of the present invention may have a minimum two dimensional area of: about 25 mm$^2$, about 20 mm$^2$, about 10 mm$^2$, or even about 5 mm$^2$.

Further embodiments of the nonwoven webs of the present invention are described below. Each embodiment is a carded spunlaced nonwoven web comprising various percentages of pulp and lyocell, or comprising the same percentages of pulp and lyocell, but with different basis weights.

To impart the discrete compressed sites of the present invention, each embodiment is compressed at different levels of compressive stress via an arrangement of a smooth calender roller and a patterned calender roller, which are both at an internal temperature of about 350° F. The pattern on the calender roller is the same as that shown in FIG. 1A and has a total raised surface area of about 12.6%. The nonwoven web is pre-moistened with about 3 grams of a silicone-based liquid composition per about 1 gram of dry web. The nonwoven web, with and without the discrete compressed sites of the present invention, is then subjected to tensile testing as describe above. The influence of compressive stress on the tensile strength of each embodiment is evident from the data in Tables 3-6.

Table 3 illustrates the influence of compressive stress on the tensile strength of a carded spunlaced nonwoven web with a nominal basis weight of about 40 grams per square meter (gsm), comprising about 50% pulp and about 50% lyocell.

It may be desirable to select the web that has been subjected to a compressive stress of 206 N/mm² for use as or in a disposable wipe since this level of compressive stress results in a significant decrease in the CD and MD maximum forces.

TABLE 3

| Embossing Cylinder Pressure [psi] | Compressive Stress [N/mm²] | CD Maximum Force [N] | CD Elongation at Maximum Force [%] | MD Maximum Force [N] | MD Elongation at Maximum Force [%] |
|---|---|---|---|---|---|
| 0 | 0 | 9.9 | 73.9 | 39.2 | 21.4 |
| 150 | 206 | 2.8 | 74.2 | 6.7 | 15.9 |
| 200 | 275 | 2.8 | 74.9 | 5.2 | 15.7 |
| 250 | 344 | 2.1 | 71.4 | 4.1 | 14.3 |
| 300 | 413 | 2.0 | 67.0 | 3.8 | 13.5 |

Table 4 illustrates the influence of compressive stress on the tensile strength of a carded spunlaced nonwoven web with a nominal basis weight of about 60 gsm, comprising about 70% pulp and about 30% lyocell.

It may be desirable to select the web that has been subjected to a compressive stress of 206 N/mm² for use as or in a disposable wipe since this level of compressive stress results in a significant decrease in the CD and MD maximum forces.

TABLE 4

| Embossing Cylinder Pressure [psi] | Compressive Stress [N/mm²] | CD Maximum Force [N] | CD Elongation at Maximum Force [%] | MD Maximum Force [N] | MD Elongation at Maximum Force [%] |
|---|---|---|---|---|---|
| 0 | 0 | 9.2 | 72.9 | 30.7 | 22.6 |
| 150 | 206 | 4.5 | 73.5 | 12.5 | 20.0 |
| 200 | 275 | 3.8 | 73.5 | 9.7 | 19.7 |
| 250 | 344 | 3.1 | 68.9 | 7.3 | 18.0 |
| 300 | 413 | 2.7 | 67.9 | 5.7 | 17.9 |

Table 5 illustrates the influence of compressive stress on the tensile strength of a carded spunlaced nonwoven web with a nominal basis weight of about 50 gsm, comprising about 40% pulp and about 60% lyocell.

It may be desirable to select the web that has been subjected to a compressive stress of 275 N/mm² for use as a disposable wipe since this level of compressive stress results in a significant decrease in the CD and MD maximum forces.

TABLE 5

| Embossing Cylinder Pressure [psi] | Compressive Stress [N/mm²] | CD Maximum Force [N] | CD Elongation at Maximum Force [%] | MD Maximum Force [N] | MD Elongation at Maximum Force [%] |
|---|---|---|---|---|---|
| 0 | 0 | 19.0 | 83.8 | 70.0 | 19.1 |
| 200 | 275 | 4.8 | 81.6 | 11.6 | 15.6 |
| 300 | 413 | 4.2 | 83.0 | 8.0 | 15.4 |

Table 6 illustrates the influence of compressive stress on the tensile strength of a carded spunlaced nonwoven web with a nominal basis weight of about 60 gsm, comprising about 40% pulp and about 60% lyocell.

It may be desirable to select the web that has been subjected to a compressive stress of 275 N/mm² for use as a disposable wipe since this level of compressive stress results in a significant decrease in the CD and MD maximum forces.

TABLE 6

| Embossing Cylinder Pressure [psi] | Compressive Stress [N/mm²] | CD Maximum Force [N] | CD Elongation at Maximum Force [%] | MD Maximum Force [N] | MD Elongation at Maximum Force [%] |
|---|---|---|---|---|---|
| 0 | 0 | 19.8 | 81.9 | 86.2 | 20.7 |
| 200 | 275 | 6.9 | 85.7 | 19.1 | 16.9 |
| 300 | 413 | 4.1 | 79.8 | 8.0 | 15.4 |

Wipes

In some embodiments of the present invention, wipes may comprise one or more layers of the web of the present invention. In further embodiments, wipes may comprise laminates of one or more layers of the web of the present invention. The wipes may be adapted for a variety of uses and may be pre-moistened or moistened with a liquid composition. The liquid composition may comprise an aqueous solution and may further comprise surfactant, co-surfactant, foam building agent, emulsifier, non-cellulosic water soluble organic polymer and mixtures thereof.

The wipes of the present invention may be suitable for use in cleaning babies, and may also find use in cleaning tasks related to persons of all ages. Such wipes may also include articles used for application of substances to the body, including but not limited to application of make-up, skin conditioners, ointments, medications and mixtures thereof. Such wipes may also include articles used for the cleaning or grooming of pets, and articles used for the general cleansing of surfaces and objects, such as household kitchen and bathroom surfaces, eyeglasses, exercise and athletic equipment, automotive surfaces and the like. Such wipes may also be used in the hospital or clinical environment to clean up bodily fluids and the like.

The wipes of the present invention may have in-use strength in at least the MD and/or the CD direction suitable for dispensing from a container of wipes. In one embodiment the wipes may be "pop-up" wipes, such that when one wipe is pulled from a container such as a tub, an edge of the next wipe in the stack may be presented for easy dispensing.

The wipes may be folded and stacked in a container such as a tub. The wipes of the present invention may be folded in any of various known folding patterns, such as C-folding and Z-folding. Use of a Z-fold pattern may enable a folded stack of wipes to be interleaved with overlapping portions. Fold patterns are disclosed more fully in commonly assigned, co-pending U.S. patent application, Ser. No. 09/344,695.

The wipes of the present invention may further comprise prints, which may provide aesthetic appeal. Non-limiting examples of prints include figures, patterns, letters, pictures and combinations thereof.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A nonwoven web having a machine direction and a cross direction, said nonwoven web comprising:
   (a) non-thermoplastic fibers comprising from about 20% to about 80% by weight of the nonwoven web of man-made fibers and from about 20% to about 80% by weight of the nonwoven web of pulp fibers, wherein at least about 20% by weight of said man-made fibers have a fiber length of at least about 18 mm;
   (b) a plurality of discrete compressed sites, each compressed site having selective breaking or weakening of fibers along edges of the compressed sites, the compressed sites are:
      i. less than about 2.5 square millimeters in area; and
      ii. separated by an edge to edge distance of no more than about 10 millimeters from the nearest adjacent discrete compressed site;
   (c) lines of weakness; and
   (d) discrete uncompressed regions, wherein said discrete uncompressed regions have an elongation at maximum force in the machine direction and an elongation at maximum force in the cross direction;
wherein said (b) plurality of discrete compressed sites form said (c) lines of weakness and said (c) lines of weakness are arranged to substantially bound and define said (d) discrete uncompressed regions, such that when said web is subjected to a force less than the maximum force of said (d) discrete uncompressed regions in at least one of said machine direction or said cross direction, said web at least partially fails in tension along said (c) lines of weakness when the nonwoven web is flushed into a plumbing system.

2. The nonwoven web according to claim 1, wherein said non-thermoplastic fibers further comprise natural fibers selected from the group consisting of: cotton, wool, silk, jute, linen, ramie, hemp, flax, camel hair, kenaf and mixtures thereof.

3. The nonwoven web according to claim 1, wherein said man-made fibers comprise rayon fibers selected from the group consisting of: viscose, lyocell and mixtures thereof.

4. The nonwoven web according to claim 1, wherein when said web at least partially fails in tension along at least one of said lines of weakness, and said discrete uncompressed regions substantially separate into discrete pieces.

5. The nonwoven web according to claim 1, wherein said non-thermoplastic fibers are not melted at said discrete compressed sites.

6. The nonwoven web according to claim 1, wherein said compressed sites are made via stamping, pressing, cold calender rolling, heated calender rolling and combinations thereof.

7. The nonwoven web according to claim 4, wherein said discrete pieces have a maximum two dimensional area of about 625 square millimeters.

8. The nonwoven web according to claim 1, wherein said web is carded spunlaced.

9. The nonwoven web according to claim 1, wherein said web is further comprised of a binder.

10. A wipe comprising said nonwoven web according to claim 1, wherein said wipe has a basis weight of from about 30 to about 150 grams per square meter.

11. The wipe according to claim 10, further wherein said wipe is pre-moistened.

12. A pre-moistened carded spunlaced nonwoven web comprising non-thermoplastic fibers comprising from about 20% to about 80% by weight of the nonwoven web of rayon fibers and from about 20% to about 80% by weight of the nonwoven web of pulp fibers, wherein at least about 20% by weight of said rayon fibers have a fiber length of at least about 18 millimeters, and further wherein said web comprises:
   (a) a plurality of discrete compressed sites, each compressed site having selective breaking or weakening of fibers along edges of the compressed sites, the compressed sites are:
      i. less than about 2.5 square millimeters in area; and
      ii. separated by an edge to edge distance of no more than about 10 millimeters from the nearest adjacent discrete compressed site;
   (b) lines of weakness; and
   (c) discrete uncompressed regions, wherein said discrete uncompressed regions have an elongation at maximum force in the machine direction and an elongation at maximum force in the cross direction;
wherein said (a) plurality of discrete compressed sites form said (c) lines of weakness and said (b) lines of weakness are arranged to substantially bound and define said (c) discrete uncompressed regions, such that when said web is subjected to a cross direction force less than about 8 Newtons, said web at least partially fails in tension along said (b) lines of weakness when the nonwoven web is flushed into a plumbing system.

13. The nonwoven web according to claim 6, wherein said calendering processes apply compressive stress to said discrete compressed sites at an amount that is greater than about 200 Newtons per square millimeter.

* * * * *